(12) United States Patent
Brookfield

(10) Patent No.: US 6,539,779 B2
(45) Date of Patent: *Apr. 1, 2003

(54) SUPPORT SYSTEM WITH RADIALLY RIGID WIRE SUSPENSION

(75) Inventor: David A. Brookfield, Sharon, MA (US)

(73) Assignee: Brookfield Engineering Laboratories, Inc., Stoughton, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/962,556

(22) Filed: Oct. 31, 1997

(65) Prior Publication Data

US 2002/0046597 A1 Apr. 25, 2002

Related U.S. Application Data

(63) Continuation of application No. 08/803,320, filed on Feb. 21, 1997, now abandoned, which is a continuation of application No. 08/365,828, filed on Dec. 29, 1994, now abandoned.

(51) Int. Cl.$^7$ ............................................... G01N 11/14
(52) U.S. Cl. ..................................... 73/54.35; 73/54.28
(58) Field of Search ............................ 73/54.28, 54.31, 73/54.32, 54.33, 54.35

(56) References Cited

U.S. PATENT DOCUMENTS

| | | | | | |
|---|---|---|---|---|---|
| 2,303,162 A | * | 11/1942 | Godwin et al. | ............. | 73/54.32 |
| 2,796,758 A | * | 6/1957 | Myers et al. | ............... | 73/54.32 |
| 2,957,339 A | * | 10/1960 | Penny et al. | ................ | 73/54.28 |
| 3,727,452 A | * | 4/1973 | Kenyon | ...................... | 73/54.35 |
| 4,175,425 A | * | 11/1979 | Brookfield | ............. | 73/54.35 X |
| 4,214,475 A | * | 7/1980 | Carter et al. | ................ | 73/54.35 |
| 5,763,766 A | * | 6/1998 | Robinson | ................... | 73/54.33 |

FOREIGN PATENT DOCUMENTS

| | | | | | |
|---|---|---|---|---|---|
| GB | 2066483 | * | 7/1981 | ................ | 73/54.33 |

* cited by examiner

Primary Examiner—Hezron Williams
Assistant Examiner—Michael Cygan
(74) Attorney, Agent, or Firm—Perkins, Smith & Cohen, LLP; Jerry Cohen

(57) ABSTRACT

The invention comprises measuring or responsive instruments, including (but not limited to) viscometers, having a music wire (20) or like high tensile wire support between driving/driven shaft assemblies (18, 16) and appropriate mounting to eliminate drag, friction, radial misalignment, vibration problems, especially at high rotational speeds, and afford an enhanced accuracy and speed of measurement or other response of the instrument as a whole, including such specific features allowing large angular deflections or small ones (full scale under one degree) and axial and radial rigidity. The instrument can also be used with a plate for cone plate, oscillation and normal force measurements.

8 Claims, 4 Drawing Sheets

SUPPORT SYSTEM WITH RADIALLY RIGID WIRE SUSPENSION

This is a continuation of application Ser. No. 08/803,320, filed Feb. 21, 1997, now abandoned which is a continuation of application Ser. No. 08/365,828, filed Dec. 29, 1994 now abandoned.

BACKGROUND OF THE INVENTION

The present invention relates to instrument systems for measuring rotational torque and is characterized by a rigid axial and radial support for the torque interconnect element.

State of the art torque interconnects such as coiled springs suffer high speed and rotational forces and weak radial alignment from significant errors introduced by wire stretching and frictional drag. Some examples of state of the art instruments are the DV-2, 3 viscometers of Brookfield Engineering Laboratories, Inc., Stoughton, Mass., U.S.A.

It is an object of the invention to overcome such difficulty.

It is a further object to provide a very high speed capability.

It is a further object of the invention to accomplish tight alignment.

It is a further object of the invention to minimize or eliminate rotational friction in a rigid support structure.

It is a further object of the invention to provide a means for dampening vibrations; such vibrations can prove detrimental to the torsional accuracy of such torsion systems.

SUMMARY OF THE INVENTION

The invention comprises measuring or responsive instruments, including (but not limited to) viscometers, having a music wire (20) or like high tensile wire support between driving/driven shaft assemblies (18, 16) and appropriate mounting to eliminate drag, friction, radial misalignment, vibration problems, especially at high rotational speeds, and afford an enhanced accuracy and speed of measurement or other response of the instrument as a whole, including such specific features allowing large angular deflections or small ones (full scale under one degree) and axial and radial rigidity. The instrument can also be used with a plate for oscillation and normal force measurements.

The invention provides a wire torsion mount of high tensile strength, e.g. music wire, a hardened steel wire with a tensile strength of 90,000 psi with an elastic modulus (E) of $27.6 \times 10^6$ psi and shearing modulus (G) in torsion of $10.6 \times 10^6$ psi. However, the invention is applicable broadly to wires with E & G values sufficiently high to provide axial support while allowing significant elastic deformation in torsional rotation. The wire avoids permanent axial deformation even when supporting axial loads of 10 pounds or more (typically 2–4 pounds in the following context of the next paragraph, but other loads in other contexts).

In the viscometer context, wires of 0.003–0.025 inch diameter wires are used, typically 0.006 inch or 0.012. Such a wire is mounted at the center of rotation of a rotational drive system of a viscometer and because of its small diameter and relatively long length (typically two inches in relation to a 0.012" diameter wire and generally over 100:1 length to diameter), has low rotational torque and essentially no centrifugal force even when rotated at high speeds. A range of torque of 0 to 10,000 dyne-cm (typically, about 7,000) is realized over a full scale angular deflection range of 45 to 90° (typically about 75°). The wire is surrounded near or at each end by a jewel bearing for radial support, thereby assuring accurate concentric alignment of the rotational drive system. Radial deflection tendencies of the torsion assembly are substantially counter-acted by the bearing.

The foregoing length to diameter considerations can be modified in certain situations, e.g. the multiple wire arrangements of certain embodiments described below. Small deflection angles can be generated using shorter lengths and/or lower length to diameter ratios (i.e. over 50:1). The smaller angle allows a lower stiffness and/or a higher sensitivity at a given stiffness or a combination of these factors.

Preferably, the wire torsional modulus and wire diameter are such as to provide a torsional resistance over an angle of less than 2° under 10,000 dyne cm.

Other objects, features and advantages will be apparent from the following detailed description of preferred embodiments taken in conjunction with the accompanying drawings in which:

DETAILED DESCRIPTION OF PREFERRED EMBODIMENTS

Figure 1:
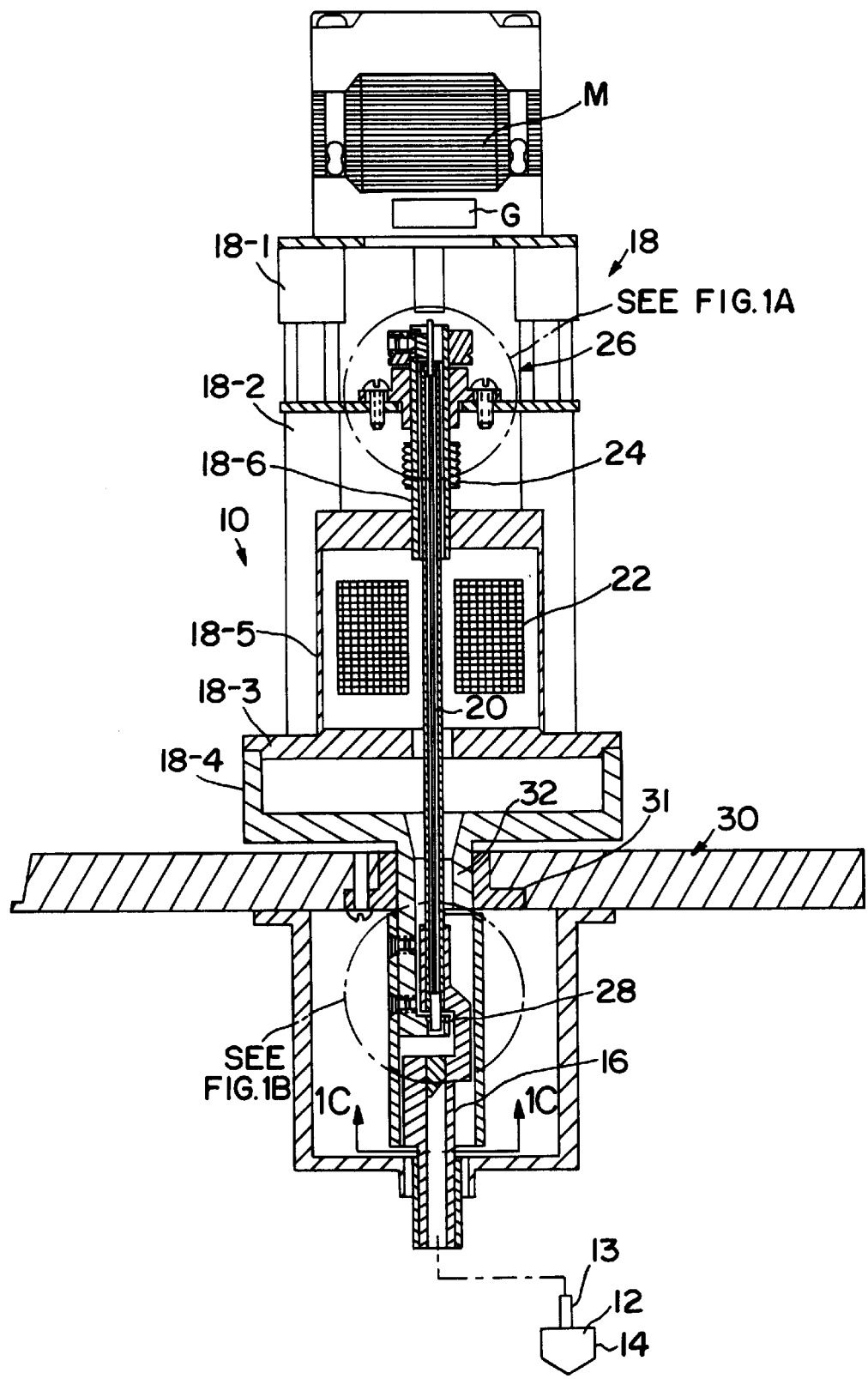
FIG. 1 is a cross-section view of a preferred embodiment of the invention.

FIG. 1 shows a viscometer instrument 10 comprising a rotational driven member 12 (spindle) with a measuring surface 14 and a support shaft 16 for interaction with the fluid to be measured. A motor M and gearing G provide high speed rotational drive to a device assembly 18 which is interconnected to the support shaft not by the usual calibrated spiral spring but rather by an elongated 2–6 inch, typically 4 inch, wire 20 made of high strength wire material, or the like, as described above. A non-limiting example of such wire is the wire type known as music wire. The effect of viscosity of a fluid encountered by the element 12 is to cause a twist of the wire 20 over an angular range of approximately 80° full scale. A read out transducer or other display or conversion device can be provided as indicated at 22, using slip rings at 24, to measure to within 0.001 or better of full scale deflection. More angular deflection allows greater sensitivity. However, it is imperative to keep the deflection well within the pure elastic range of the wire material.

Figure 1A:
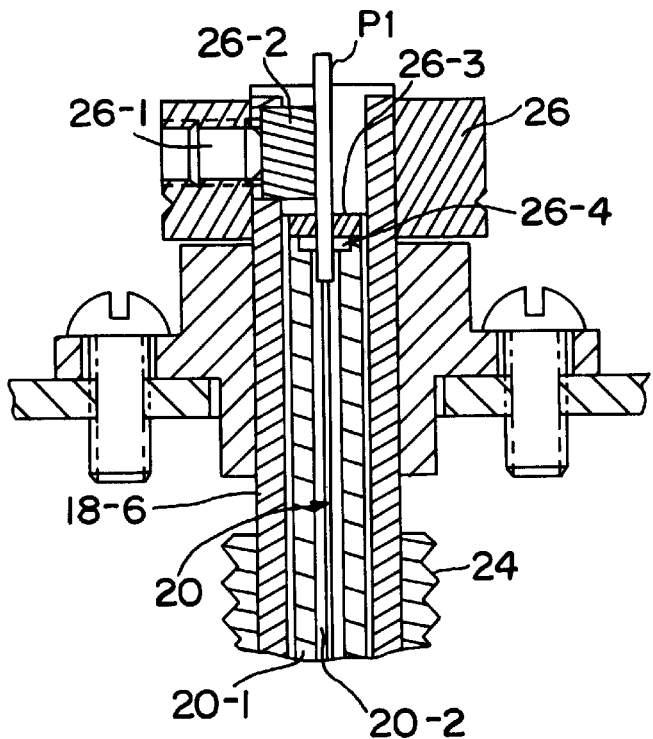
FIGS. 1A and 1B are expanded sectional views of upper and lower mount portions thereof and FIG. 1C is a lateral cross-section view taken as indicated at C—C in FIG. 1.
Figure 1C:
Figure 1B:
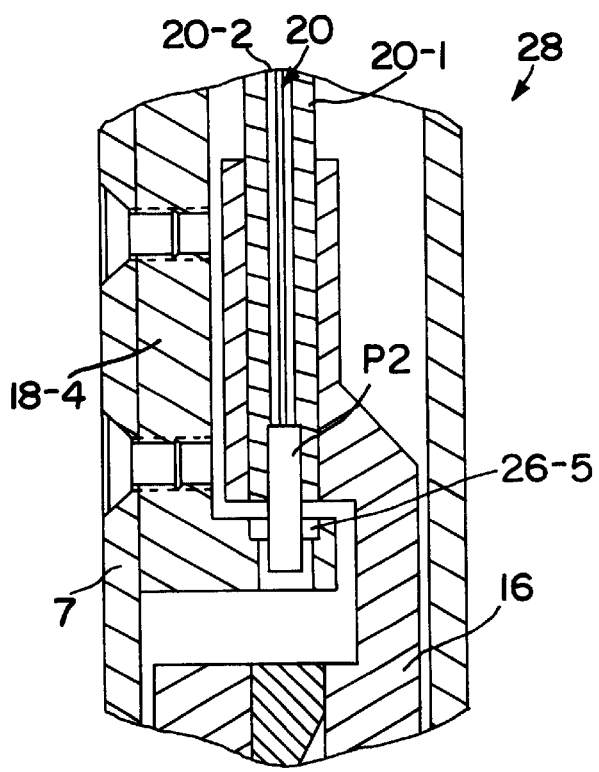

The wire is held in mounting pins P between a top mount 26 and bottom mount 28. The top mount, shown in FIG. 1A includes a set screw 26-1 which can be loosened and retightened for setting a zero angle setting. A block (26-2) locked to the drive train acts as a non-destructive clamp for the upper end of the wire assembly. A ring 26-3 is glued or fitted to the wire, to act as a stop for axial positioning and control of upward movement of tube 20-1, typically limiting movement to 0.003–005". The bottom mount (FIG. 1B) comprises the music wire pressed in a 0.062" diameter pin P with an appropriate bore to receive the wire. A rotatable tube 20-1 surrounds and is rotatably held with wire 20. The annulus (20-2) between the wire and tube can be filled with a damping fluid (e.g. a high viscosity silicone oil or similar fluids). The top pin P1 (FIG. 1A) is in a jewel bearing 26-4 under the stop 26-3 and the lower pin P (FIG. 1B) is in a jewel bearing 26-5. A tube 18-6 surrounds tube 20-1 for part but not all its length (FIGS. 1, 1A) and the slip rings 24 are on its outer surface. It can be seen that due to clamping (via 26-1, 26-2) of upper pin P1 and non-clamping of lower pin P2, a twisting force applied by the spindle 12 (a rotating load) via shaft 16 to the array can in turn apply a torque that is transmitted to wire 20 at its bottom end at P2, but not at its top end where the pin P1 is clamped. The rotating drive structure as a whole comprises the power train M, G and a two part rotatable drive, comprising (a) tubular shaft 16, and tube 20-1, and (b) the structure 18 (including 18-1, 18-2, 18-3, 18-4, 18-5 and 18-6) wherein one of the parts is suspended from the other via wire 20 (specifically in FIGS. 1, 1A, 1B, 1C, 16 being suspended from 18 via the wire).

A fixed structure plate 30 of the instrument accommodates a necked down section 32 of the rotating assembly for rotation within a bearing or bushing 31.

The rotating assembly as a whole has an axially and radially rigid suspension, does not require axial bearings for the critical wire 20 or tube 20-1 (bushing 31 does not detract from sensitivity) and is a breakthrough in sensitive suspension design. The top and bottom mounts of the wire hold it rigid radially, but do not interfere circumferentially and provide for rigid and substantial axial support.

Because tube 7 surrounds sensing shaft 16 and is connected rigidly to the driven shaft 18-4, the non-symmetrical section of the rotating sensing shaft assembly is covered by likewise rotating portions thereby eliminating air turbulence and windage effects at high rotational speeds.

As mentioned above the torsional assembly, as a whole, is useful in viscometers and other instruments (e.g. dial displays of volt-meters, ammeters and other electrometers), magnetism sensors and torque sensors in general and in non-instrument contexts (e.g. motors for clockwork, displays, vane supports pointers). The latter is a driven (tubular) shaft locked to shaft 16 at the lower end. The drive or driver components include 18-1, 18-2, 18-3, 18-4 all driven directly by M/G and driving shaft 16 subject to angular deflection therebetween taken up at twisted wire 20.

Figure 2:
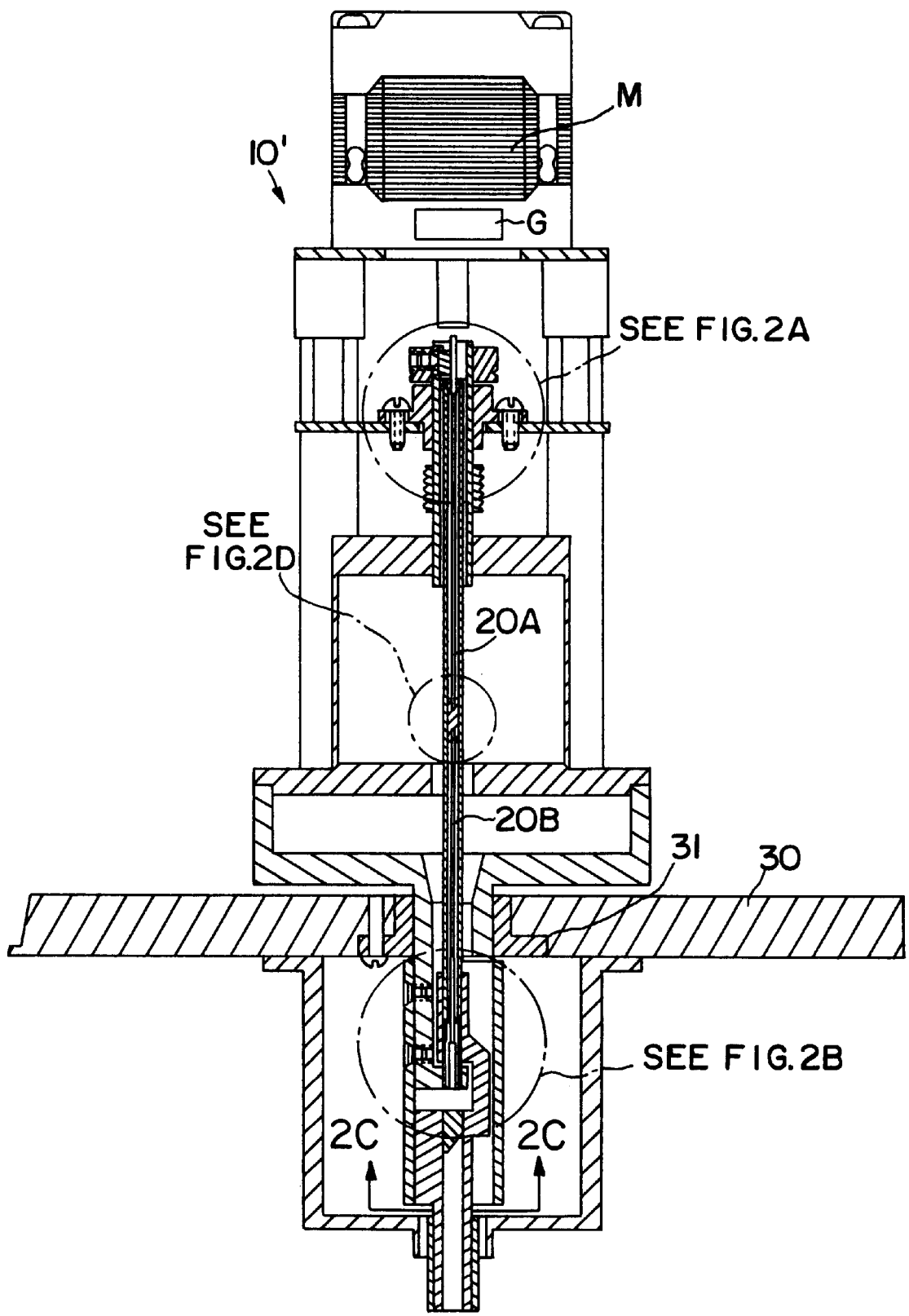
FIG. 2 is a cross-section view of another preferred embodiment utilizing multiple linked wires, FIGS. 2A, 2B and 2C as applied to FIG. 2 correspond to FIGS. 1A, 1B, 1C
Figure 2A:
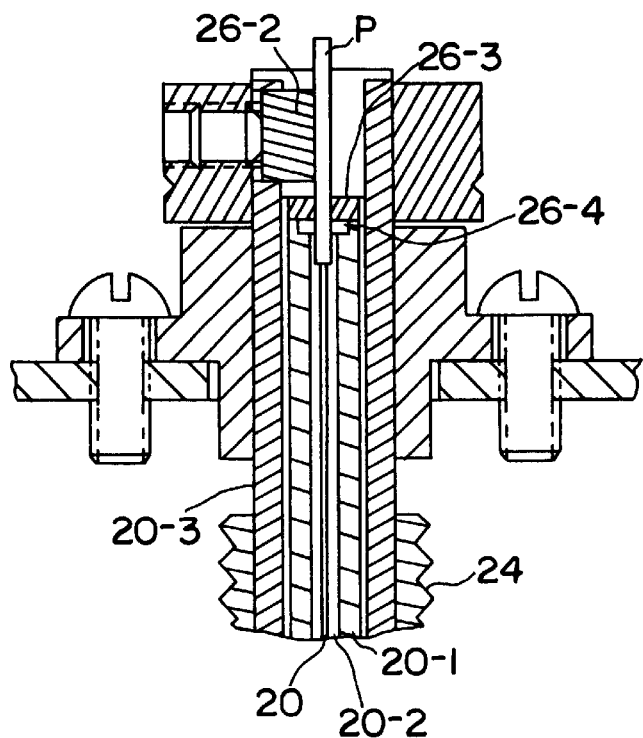
FIG. 2D is an expanded view of the wire link.
Figure 2C:
Figure 2B:
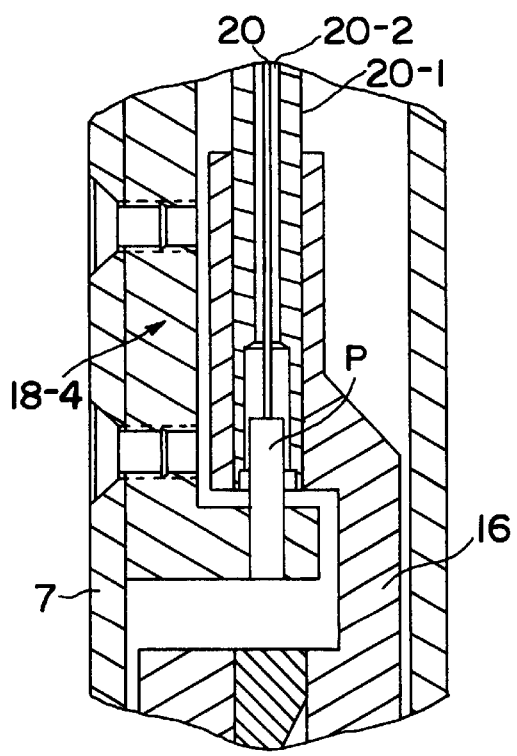
Figure 2D:
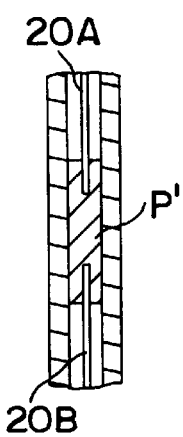

The further preferred embodiment of an instrument 10' shown in FIGS. 2, 2A, 2B, 2C, 2D is identical to the FIG. 1 embodiment with the important difference that the wire 20 is subdivided into sections 20A, 20B with meeting ends fixed in a middle pin P'. This arrangement has the advantage that both ends of the support wire assembly are fixed to the driven portion 18-4 with the wire jewel bearing supports mounted on the sensing shaft 20-1. Axial play is thus totally eliminated with no loss in sensitivity or increase in friction. However, this arrangement does provide greater rotational stiffness and will require smaller wire sizes and/or lesser angles of deflection for full scale. One major advantage herein is it enables a rheogram instrument providing quick, continuous tracking of rheological properties at varying rotational speeds without the need for settling in time at each new speed setting. For a given wire diameter halving the length (dividing it in two as shown at FIG. 2D) affords a 4× stiffness enhancement. The wire assembly of FIG. 2 flexes, but is fully locked against axial movement (compared to slight axial play in FIG. 1).

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A rotational instrument with rigid radial and axial support comprising:
   (a) means for supporting a sensing element for rotation;
   (b) said means for supporting having a two part rotatable structure with a substantially vertical axis of rotation comprising a first drive part and second sensing part with one part suspended vertically from the other via a torsional wire extending centrally within said rotatable structure along said axis of rotation thereof, with one end of the wire fixedly connected to one part of the said rotatable structure and the other wire end connected to other part of the rotatable structure and means for rigid radial alignment of the two parts of the rotatable structure such that they maintain accurate concentric alignment;
   (c) means for rotationally driving the rotatable structure;
   (d) means for providing a fixed axial spacing between the connections of the wire to the support structure portions,
   (e) the wire providing a low torsional resistance but high axial strength so that the axial load of the sensing element is carried axially in the wire, but torque transmitted from the sensing element results in a measurable twisting of the wire, the means for axial spacing comprising a tube surrounding the wire; and wherein
   (f) a damping fluid is provided between the support structure and the wire to reduce vibration and noise on the wire at high rotational speeds and/or from rough driving means.

2. A rotational instrument with rigid radial and axial support comprising:
   (a) means for supporting a sensing element for rotation;
   (b) said means having a two part rotatable structure with a substantially vertical axis of rotation comprising a first drive part and second sensing part with one part suspended vertically from the other via a torsional wire extending centrally within said rotatable structure along axis of rotation thereof, with one end of the wire fixedly connected to one part of the said rotatable structure and other wire end connected to other part of the rotatable structure and means for rigid radial alignment of the two parts of rotatable structure such that they maintain accurate concentric alignment;
   (c) means for driving the rotatable drive structure;
   (d) means for providing a fixed axial spacing between the connections of the wire to the support structure portions;
   (e) the wire providing a low torsional resistance but high axial strength so that the axial load of the sensing element is carried axially in the wire, but torque transmitted from the sensing element results in a measurable twisting of the wire, the means for axial spacing comprising a tube surrounding the wire; and wherein
   (f) the instrument is configured as a viscometer and further comprising:
   (g) sensing means supported by the support means constructed and arranged for interacting in rotary shear with a fluid whose viscosity to be measured; and
   (h) means for measuring twisting deflection of the wire as a read out of fluid viscosity; and wherein
   (i) a damping fluid is provided between the tube and the wire to reduce vibration and noise on the wire at high rotational speeds and/or from rough driving means.

3. A rotational instrument for viscosity measurement with rigid radial and axial support comprising:

(a) means comprising a two part rotatable structure for supporting a sensing element for rotation;

(b) said means for supporting having drive and sensing structure parts with the sensing part suspended from the driving part via a torsional wire extending centrally within the rotatable sensing structure along a common vertical axis of rotation thereof, with an upper end of the wire fixedly connected, without bearings, to an upper part of the rotatable structure and the lower wire end fixedly connected, without bearings, to the sensing part of the rotatable structure and means for maintenance of rigid radial alignment of the two parts of the rotatable structure such that they maintain accurate concentric alignment through the suspension of the sensing part from the driving part and radially clamped upper and lower connections therebetween;

(c) means for driving the rotatable structure so that the wire rotates with the rest of said structure and kind relative movement therebetween so that the wire rotates with the rest of said structure and kind relative movement therebetween;

(d) means for providing a fixed axial spacing between the connections of the wire to the support structure portions;

(e) the wire providing a low torsional resistance but high axial strength so that the axial load of the sensing element is carried axially in the wire, but torque transmitted from the sensing element results in a measurable twisting of the wire, (f) the means for axial spacing comprising a tube surrounding the wire and (g) the means for extracting continuous measurement of wire twist, correlatable to viscosity throughout each resolution, as the assembly rotates.

4. The instrument of claim 3, configured as a viscometer and further comprising:

g) sensing means supported by the support means constructed and arranged for interacting in rotary shear with a fluid whose viscosity to be measured; and h) means for measuring twisting deflection of the wire as a read out of fluid viscosity so that the wire rotates with the rest of said structure to provide relative movement therebetween.

5. The instrument of either of claims 3 or 4 wherein the wire torsional modulus and wire diameter are such as to provide a torsional resistance over an angle of 45° or more, under 10,000 dyne-cm.

6. A rotational instrument with rapid radial and axial support comprising a wire wherein the wire having at least two segments end to end with a fixed connection to each other and a surrounding tube at the meeting ends of the wire segments, together with (a) means for supporting a sensing element for rotation;

(b) said support means having a two part rotatable drive and sensing structure with one part suspended from the other via a torsional wire extending centrally within a rotatable sensing structure along an axis of rotation thereof, with one end of the wire fixedly connected, without bearings, to one part of the rotatable structure and the other wire end fixedly connected, without bearings, to other part of the rotatable structure and means for rigid radial alignment of the two parts of the rotatable structure such that they maintain accurate concentric alignment;

(c) means for driving the rotatable structure so that the wire rotates with the rest of said structure and kind relative movement therebetween;

(d) means for providing a fixed axial spacing between the connections of the wire to the support structure portions, and;

(e) the wire providing a low torsional resistance but high axial strength so that the axial load of the sensing element is carried axially in the wire, but torque transmitted from the sensing element results in a measurable twisting of the wire, the means for axial spacing comprising a tube surrounding the wire.

7. The instrument of claim 6 wherein the wire has at least two segments end to end with a fixed connection to each other and the surrounding tube at the meeting ends of the wire segments configured as a viscometer and further comprising:

(g) sensing means supported by the support means constructed and arranged for interacting in rotary shear with a fluid whose viscosity to be measured; and (h) means for measuring twisting deflection of the wire as a read out of fluid viscosity.

8. The instrument of either of claims 6 or 7 wherein the wire torsional modulus and wire diameter are such as to provide a torsional resistance over an angle 45° or more, under 10,000 dyne cm.

* * * * *